United States Patent [19]

Sloviter

[11] 4,397,870

[45] Aug. 9, 1983

[54] PROCESS FOR PROLONGING RETENTION OF EMULSION PARTICLES IN THE BLOODSTREAM

[75] Inventor: Henry A. Sloviter, Philadelphia, Pa.

[73] Assignee: The University of Pennsylvania, Philadelphia, Pa.

[21] Appl. No.: 402,449

[22] Filed: Jul. 27, 1982

[51] Int. Cl.³ .................... A61K 31/13; A61K 31/02
[52] U.S. Cl. .................................. 424/325; 424/199; 424/350; 424/358; 424/365
[58] Field of Search ............... 424/325, 350, 358, 365, 424/199

[56] References Cited

U.S. PATENT DOCUMENTS 3,958,014  5/1976  Watanabe et al. .
3,962,439  6/1976  Yokoyama et al. .
4,105,798  2/1981  Moore et al. .
4,133,874  1/1979  Miller et al. .
4,252,827  2/1981  Yokoyama et al. .

Primary Examiner—Sam Rosen
Attorney, Agent, or Firm—Seidel, Gonda & Goldhammer

[57] ABSTRACT

The retention of coated particles previously infused into the bloodstream of animals may be prolonged by one or more injections of coating substance. For example, the retention of an artificial blood composition comprising emulsified lecithin-coated perfluoro compounds may be prolonged by injection of lecithin.

15 Claims, No Drawings

PROCESS FOR PROLONGING RETENTION OF EMULSION PARTICLES IN THE BLOODSTREAM

BACKGROUND OF THE INVENTION

Natural whole blood is in short supply, and the shortage will probably increase. New methods for prolonged preservation of blood in the frozen state and improvements in storage in the liquid state have resulted in more efficient use of available blood in some areas, but the world-wide need for blood for transfusion still far exceeds the supply. Since it is unlikely that there will be any appreciable increase in supply, needs must be satisfied by substances other than natural blood or its derivatives. An artificial blood, available in unlimited quantities and free from infectious agents and antigens would be an extremely valuable therapeutic agent.

Emulsions of perfluoro compounds now seem likely to be successful as artificial blood. Perfluorochemical emulsion artificial bloods are free of infectious agents and antigens. (Hereinafter, perfluoro compound and perfluorochemical shall be used interchangeably). Blood typing of the recipient is unnecessary. However, such artificial bloods lack clotting factors, platelets, immunoglobulins and antibodies.

Perfluorochemical emulsions have been sucessfully as substitutes for red blood cells in perfusing isolated animal organs and in the delivery of oxygen to the tissues of intact animals. Recently, an emulsion of perfluorochemicals was used in treating human subjects.

Although perfluoro compounds are chemically inert, they may adversely affect blood platelets and blood coagulation factors, resulting in thrombocytopenia (i.e., decrease in the absolute number of blood platelets) and disorders of blood coagulation. It has been found that the effects on platelets are likely due to unusual surface properties of perfluoro compounds, namely a very low surface tension. This effect can be overcome by coating the perfluoro compound particles with a substance which masks its surface activity.

Among the prior patents pertaining to artificial blood compositions the following are noted:

Miller et al, U.S. Pat. No. 4,133,874 is directed to water-soluble lipid-encapsulated hemoglobin.

Watanabe et al, U.S. Pat. No. 3,958,014; Yokoyama et al, U.S. Pat. No. 3,962,439; Moore et al, U.S. Pat. No. 4,105,798; and Yokoyama et al U.S. Pat. No. 4,252,827 pertain to emulsified oxygen-transporting particles of perfluoro compounds.

Prior artificial bloods have limited duration in the bloodstream. Within 2-4 days after transfusion of emulsified perfluoro compound particles, virtually all particles disappear from the circulation. Moreover, thrombocytopenia is often observed in laboratory animals after infusion. What is needed is a method for extending the effective life of the artificial blood composition in circulation.

An important problem concerning the clinical use of perfluoro compound emulsions is the retention of perfluoro compound in the tissues, mainly the liver and the spleen. The major route of perfluoro compound elimination is through the lungs. An increase in the time which the material remains in circulation results in increased elimination as expired gas, and hence a decrease in retention in the liver and spleen.

SUMMARY OF THE INVENTION

The present invention provides for the prolongation of effective artificial blood levels in the circulation up to fourteen days or more after infusion. By maintaining a relatively high continuous level of the coating substance in the blood plasma, the removal of the coating of artificial blood particles is apparently slowed. A high continuous level of coating substance in the blood plasma is maintained by periodic injection of coating substance following infusion of the artificial blood.

The present invention is a process for prolonging the in vivo stability and retention of coated water-insoluble particles in the bloodstream of animals, including humans, comprising one or more injections of the same coating substance which coats the water-insoluble particles.

According to the invention, the effective life of an artificial blood emulsion, particularly lecithin-coated perfluoro compounds, can be prolonged in the blood circulation of animals into which the artificial blood has been infused. Increased retention of perfluoro compounds in the circulation also results in decreased retention in the liver and spleen.

DETAILED DESCRIPTION OF THE INVENTION

Coated particles are introduced into the bloodstream of animals, including humans. The duration of effective particle levels in the bloodstream is brief, owing to the apparent removal of the coating and exposure of particle surfaces in the bloodstream. According to the present invention, the patient who has previously received an infusion of an emulsion of coated particles receives an injection one or more times with coating substance, i.e., the same substance which forms the coating surrounding the infused particles.

The most notable application of the present invention lies in the prolongation of effective artificial blood levels in the circulation. Artificial blood compositions comprise emulsions of perfluorochemicals. Perfluorochemicals have the ability to transport oxygen. However, because of the effect of perfluorochemicals on platelets, they must be coated. When a lipid or other coating substance is used to form a coating around perfluorochemical particles, retention of the particles in circulation is achieved according to the present invention by injection of the lipid or coating substance alone.

The present invention is demonstrated on artificial bloods wherein the coating substance also acts as emulsifier for the perfluorochemical particles; thereby dispensing with a separate emulsifier. Artificial blood compositions may also comprise emulsified perfluorochemical particles coated with a substance different from the emulsifier. Retention of these artificial blood compositions in circulation is achieved by injection of the coating substance.

The specific emulsifier employed must be nontoxic. High molecular weight, nonionic surfactants have been used including various polyoxyethylenes, polyoxypropylenes and co-polymers thereof available commercially under the trademark "Pluronic" of BASF-Wyandotte Corp. Lipids, most notably lecithin from egg yolk phospholipid are generally preferred. Lecithin is also available as soybean phosphalipid, but due to the need for purification of soybean phosphalipid, the egg yolk source is preferred.

Lecithin is preferred as a coating substance and emulsifier since it will not be rejected by the infusion recipient. The lecithin coating will appear to the circulation as the membrane of a natural erythrocyte. Lecithin is nontoxic and does not effect blood coagulation.

Artificial blood compositions are contained in physiologically acceptable media. Physiologically acceptable media include, but are not limited to, isotonic solutions such as Tyrode solution, Ringer's solution, lactated Ringer's solution, or Ringer's solution containing glucose. Some compositions additionally contain an emulsifier adjuvant such as traces of fatty acid.

The injections of the present invention may be administered by any injection route. In small laboratory animals such as rats the intraperitoneal route is preferred. In humans the intramuscular route is preferred.

The coating substance to be injected may be suspended in one of the above physiologically acceptable media. Tyrode solution is preferred. The injection should contain a concentration of coating substance to bring about the desired level of emulsion retention in the circulation.

The present invention is preferably carried out after infusion of an artificial blood emulsion comprising perfluorochemical particles coated with adherent lecithin in the amount of 50–70 umols/ml of perfluorochemical. Such emulsion contains about 15–40% (v/v) perfluoro compound, corresponding to about 30–75% (w/v), and about 7–9% (w/v) lecithin.

The present process for prolonging retention of emulsified particles in the bloodstream, although applicable to a wide range of emulsions, will be demonstrated without limitation on an artificial blood composition comprising a lecithin emulsion of perfluorotripropylamine. Other suitable perfluoro compounds are exemplified by, but not limited to, perfluorodecalin, perfluoromethyldecalin, and perfluorotributylamine. Emulsions of this type are described in my copending application Ser. No. 402,451, filed on even date herewith and entitled "Perfluorochemical Emulsion Artificial Blood".

PREPARATION OF LECITHIN EMULSION OF PERFLUOROTRIPROPYLAMINE

To 7 ml of cold Tyrode solution (pH 7.4) in a Rosette cell was added 960 mg of purified lecithin (derived from egg yolks). The mixture was sonicated at 110 watts for 15 sec. Sonication was repeated once after an interval of 1 min. To this dispersed lecithin in a Rosette cell at 0° C., was added 4 ml of perfluorotripropylamine, and the mixture was sonicated as before for eight 15 sec. periods with an interval of 1 minute after each sonication. The resulting milky white emulsion was centrifuged at 4° C. for 60 minutes at 100×g to sediment any large particles. The bottom 5% of the emulsion was discarded. The emulsion contained 35–40% (v/v) dispersed perfluoro compound, and its pH was between 7.35 and 7.40. The emulsified perfluoro particles were about 0.1 um in diameter and contained 50–70 umols of lecithin per ml of perfluoro compound.

The lecithin content of the perfluoro particles was measured by twice washing the sedimented particles from an aliquot of the emulsion with Tyrode solution, extracting the lecithin with a mixture of chloroform and methanol, and determining the phosphorus content of the extract. The amount of lecithin present, measured in micromoles, is calculated by dividing the phosphorus content in micrograms by a factor of 31 (the atomic weight of phosphorus). This calculation yields the micromoles of lecithin since one molecule of lecithin contains one phosphorus atom.

The above perfluorotripropylamine emulsion was infused into rats as follows.

INFUSION OF PERFLUOROTRIPROPYLAMINE EMULSION INTO RATS

Four groups of male Sprague-Dawley rats (200–250 g) anesthetised with pentobarbital (30 mg/kg) received 8 to 10 ml of emulsion infused per rat by a pump into the femoral vein at 0.2 ml/min. An approximately equal volume of blood was withdrawn during the infusion. Group 1 (Table I) received a "No Excess Lecithin" emulsion-preparation which was sedimented, washed to remove excess lecithin, and resuspended in 8% bovine serum albumin in Tyrode solution. Groups 2–4 (Table I) received an "Excess Lecithin" emulsion-preparation containing about 0.5 g of lecithin in the aqueous phase of the emulsion.

Samples were obtained at intervals after infusion for measurement of hematocrit, concentration of perfluorotripropylamine and platelet count. The concentration of perfluorotripropylamine in the blood of rats at the completion of infusion was in the range of 19–22% (v/v). In Group 4, designated as "high F-Crit", these values were in the range of 24–28% (v/v). By analogy to the term hematocrit, the term "F-Crit" has been used to designate the percentage (v/v) of emulsified perfluoro compound in the circulating blood.

EFFECT OF LECITHIN INJECTION ON RETENTION OF LECITHIN-EMULSIFIED PERFLUOROTRIPROPYLAMINE IN THE CIRCULATION

Groups 1 and 2 received a daily intraperitoneal injection of Tyrode solution. Group 3 received a daily injection of 1 g of lecithin dispersed by sonication in Tyrode solution. Group 4 rats were the same as in Group 3, except that the initial concentration of emulsified perfluorotripropylamine in the blood was higher. Blood samples were taken from each rat every day just before the injection of lecithin for measurement of the amount of perfluorotripropylamine in the circulation. The presence of a relatively high concentration of lecithin in the blood plasma was determined by thin-layer chromatography.

Results are tabulated in Table I. All values in Table I are mean±SEM. The values in parentheses in Table I below F-Crit values for 48 hr and 96 hr represent the proportion each respective F-Crit value bears to the F-Crit at 10 minutes after infusion.

The results in Table I show that daily injections of lecithin caused large increases in the amount of emulsified perfluorotripropylamine retained in the circulation, e.g., 67% retained at 96 hours compared to 3% for rats which did not receive lecithin injections. The duration of retention of emulsified perfluorotripropylamine in the circulation increased from 4 days for rats not injected with lecithin (Groups 1 and 2), to 10 days for rats injected with lecithin (Group 3), and to 14 days for rats injected with a higher initial concentration of perfluorotripropylamine (Group 4).

In all four groups of rats, platelet count after infusion of perfluorotripropylamine were not significantly different from counts obtained before infusion (See Table I). In control rats which received no perfluorotripropylamine infusion, but which received daily lecithin injections, there were no significant changes in platelet counts. All rats, comprising four experimental groups and controls, remained in good health and were normally active. The plasma of all rats receiving daily lecithin injections was opalescent and chromatographically positive for lecithin twenty four hours after lecithin was injected.

Thus, a large increase in the retention of lecithin-coated emulsified perfluoro compound in the circulation may be achieved by maintaining a high concentration of lecithin in the plasma. These results support the conclusion that lecithin-coated particles of perfluoro compounds are phagocytosed after much or all of its lecithin has been removed.

In the absence of daily injections of lecithin, complete removal of perfluoro compounds from the circulation takes place in 3-4 days. In these rats the half life of perfluoro compound in the tissues is much longer than in rats injected with lecithin. It has been reported that the half-life of emulsified perfluorotripropylamine in rat tissues is 60 days. Prolonged retention of perfluoro compound emulsion in the circulation results in increased elimination of perfluoro compound in expired gas from the lungs. Retention in the tissues, notably the liver and spleen, is thereby reduced. Those rats receiving daily lecithin injections exhibited a perfluorotripropylamine tissue half-life of about 10 days, as compared to 60 days in the absence of the lecithin-injection regimen.

TABLE I

Effect Of Lecithin Injection On Retention Of Lecithin-Emulsified Perfluorotripropylamine In The Circulation of Rats

| Preparation | No. of Rats | F-Crit, Time after Infusion | | | Days from Infusion to Zero F-Crit | Before Infusion | Platelet Count × $10^{-3} \mu l^{-1}$ After Infusion | | |
|---|---|---|---|---|---|---|---|---|---|
| | | 10 min | 48 hr | 96 hr | | | 10 min | 48 hr | 96 hr |
| Group 1: No Excess Lecithin | 8 | 20 ± 0.5 (100%) | 5 ± 0.9 (25%) | 0 (0%) | 3 | 730 ± 40 | 690 ± 60 | 630 ± 70 | 720 ± 50 |
| Group 2: Excess Lecithin | 18 | 21 ± 0.4 (100%) | 12 ± 0.4 (57%) | 3 ± 0.4 (14%) | 4 | 690 ± 20 | 680 ± 20 | 680 ± 20 | 720 ± 30 |
| Group 3: Lecithin Injected 1 g/day | 18 | 21 ± 0.3 (100%) | 18 ± 0.5 (86%) | 14 ± 0.4 (67%) | 10 | 650 ± 20 | 610 ± 20 | 610 ± 20 | 650 ± 20 |
| Group 4: High F-Crit, Lecithin Injected 1 g/day | 6 | 26 ± 0.5 (100%) | 21 ± 0.3 (81%) | 19 ± 1.0 (73%) | 14 | 680 ± 20 | 640 ± 30 | 600 ± 30 | 640 ± 20 |

The data indicate that the present invention contributes to the safety and efficacy of artificial blood. Prolonged retention of the perfluoro compound in the circulation increases the duration of transport and delivery of oxygen to the tissues. Decreased retention of the perfluoro-compound in the body tissues reduces the hazard of carcinogenic or other chronic toxic action on the tissues.

The present process for prolonging retention of emulsified particles in the circulation by maintaining a high plasma level of the substance which coats the particle is believed applicable to any emulsion of any perfluoro compound. For example, the retention of artificial bloods or oxygen-transfer particles emulsified with various surfactants, such as the "Pluronic" surfactants, may be prolonged by injections of the particular surfactant coating used on the particles. Moreover, the present process is believed to have broader application in prolonging retention in the circulation of other emulsion systems, not just artificial blood compositions.

The present invention may be embodied in other specific forms without departing from the spirit or essential attributes thereof and, accordingly, reference should be made to the appended claims, rather than to the foregoing specification, as indicating the scope of the invention.

I claim:

1. A process for prolonging the stability and retention of coated water insoluble oxygen transporting particles infused into the bloodstream of animals and humans comprising at least one subsequent injection of the same substance which coats the infused particles.

2. A process according to claim 1 wherein the infused particles are present in an emulsion in which the emulsifier is a different substance than the particle-coating substance.

3. A process according to claim 1 wherein the infused particles comprise artificial blood.

4. A process according to claim 3 wherein the artificial blood is an emulsion comprising an oxygen-transporting perfluoro compound, an emulsifier which coats the perfluoro compound, and a physiologically acceptable medium.

5. A process according to claim 4 wherein the artificial blood composition additionally contains a fatty acid emulsifier adjuvant.

6. A process according to claim 3 wherein the perfluoro compound is selected from the group consisting of perfluorodecalin, perfluoromethyldecalin, perfluorotripropylamine, and perfluorotributylamine.

7. A process according to claim 4 wherein the emulsifier is selected from the group consisting of lipid and high molecular weight nonionic surfactants.

8. A process according to claim 7 wherein the emulsifier is a phosphalipid.

9. A process according to claim 8 wherein the emulsifier is lecithin.

10. A process according to claim 7 wherein the emulsifier is a polyoxyethylene-polyoxypropylene copolymer.

11. A process according to claim 7 wherein the amount of perfluoro compound in the infused emulsion is up to about 75% (w/v).

12. A process according to claim 7 wherein the amount of emulsifier in the infused emulsion is about 7-9% (w/v).

13. A process according to claim 7 wherein the physiologically acceptable medium is isotonic solution.

14. A process according to claim 13 wherein the isotonic solution as selected from the group consisting of Tyrode solution, Ringer's solution, lactated Ringer's solution, and Ringer's solution containing glucose.

15. A process for prolonging the stability and retention of a perfluoro compound emulsion in the circulation useful as an artificial blood containing about 30-75% (w/v) perfluoro compound and about 7-9% (w/v) lecithin comprising at least one subsequent injection of lecithin into the circulation.

* * * * *